United States Patent [19]
Riese et al.

[11] Patent Number: 5,865,248
[45] Date of Patent: Feb. 2, 1999

[54] CHEMICALLY INDUCED PERMEABILITY ENHANCEMENT OF SUBTERRANEAN COAL FORMATION

[75] Inventors: Walter C. Riese, Katy; Stephen V. Bross, Sugar Land, both of Tex.

[73] Assignee: Vastar Resources, Inc., Houston, Tex.

[21] Appl. No.: 846,994

[22] Filed: Apr. 30, 1997

Related U.S. Application Data

[63] Continuation-in-part of Ser. No. 594,725, Jan. 31, 1996, Pat. No. 5,669,444.

[51] Int. Cl.[6] .......................... E21B 43/17; E21B 43/25; E21B 43/26; E21B 43/30
[52] U.S. Cl. .................. 166/263; 166/245; 166/271; 166/305.1; 166/308
[58] Field of Search ................... 166/245, 263, 166/268, 401, 305.1, 308; 299/12, 16

[56] References Cited

U.S. PATENT DOCUMENTS

| | | | |
|---|---|---|---|
| 3,856,084 | 12/1974 | Parsons | 166/257 |
| 3,952,802 | 4/1976 | Terry | 166/262 |
| 3,999,607 | 12/1976 | Pennington et al. | 166/259 |
| 4,032,193 | 6/1977 | Drinkard et al. | 299/4 |
| 4,043,395 | 8/1977 | Every et al. | 166/263 |
| 4,243,101 | 1/1981 | Grupping | 166/261 |
| 4,245,699 | 1/1981 | Steeman et al. | 166/271 |
| 4,424,863 | 1/1984 | White | 166/268 |
| 4,537,252 | 8/1985 | Puri et al. | 166/272 |
| 4,662,439 | 5/1987 | Puri et al. | 166/272 |
| 4,662,443 | 5/1987 | Puri et al. | 166/261 |
| 4,747,642 | 5/1988 | Gash | 166/256 |
| 4,756,367 | 7/1988 | Puri et al. | 166/263 |
| 4,762,543 | 8/1988 | Pantermuuehl et al. | 62/28 |
| 4,765,407 | 8/1988 | Yuvancic | 166/268 |
| 4,833,170 | 5/1989 | Agee | 518/703 |
| 4,883,122 | 11/1989 | Puri et al. | 166/263 |
| 4,913,237 | 4/1990 | Kutas | 166/308 |
| 4,973,453 | 11/1990 | Agee | 422/190 |
| 4,993,491 | 2/1991 | Palmer et al. | 166/280 |
| 5,014,785 | 5/1991 | Puri et al. | 166/263 |
| 5,014,788 | 5/1991 | Puri et al. | 166/280 |
| 5,048,328 | 9/1991 | Puri | 73/153 |
| 5,085,274 | 2/1992 | Puri et al. | 166/252 |
| 5,099,921 | 3/1992 | Puri et al. | 166/266 |
| 5,133,406 | 7/1992 | Puri | 166/266 |
| 5,332,036 | 7/1994 | Shirley et al. | 166/268 |
| 5,388,640 | 2/1995 | Puri et al. | 166/263 |
| 5,388,641 | 2/1995 | Yee et al. | 166/263 |
| 5,388,642 | 2/1995 | Puri et al. | 166/266 |
| 5,388,643 | 2/1995 | Yee et al. | 166/266 |
| 5,388,645 | 2/1995 | Puri et al. | 166/268 |
| 5,416,286 | 5/1995 | Palmer et al. | 166/268 |

(List continued on next page.)

OTHER PUBLICATIONS

SPE 20732 paper entitled "Enhanced Coalbed Methane Recovery", R. Puri and D. Yee, presented at the 65th Annual Technical Conference and Exhibition of the Society of Petroleum Engineers, New Orleans, LA, Sep. 23–26, 1990.

"Multicomponent high–pressure adsorption equilibria on carbon substrates: theory and data", *Fluid Phase Equilibria*, 78 (1992) 99–137 pp.; Elsevier Science Publishers, B.V., Amsterdam.

"Openhole Cavity Completions in Coalbed Methane Wells in the San Juan Basis" I.D. Palmer, Amoco Production Co.: M.J. Mavor, Resource Enterprises Inc.; J.P. Seidle, J.L. Spitler, and R.F. Volz, Amoco Production Co.

*Primary Examiner*—George Suchfield
*Attorney, Agent, or Firm*—F. Lindsey Scott

[57] ABSTRACT

A method for increasing the permeability to methane of a subterranean coal formation by chemically stimulating the coal formation by injecting a gaseous oxidant into the coal formation and thereafter producing methane from the coal formation at an increased rate. The gaseous oxidant is ozone, oxygen or combinations thereof. The completion of wells penetrating a subterranean coal formation is facilitated by injecting a gaseous oxidant into the coal formation surrounding the well prior to forming a cavity in the coal formation around the well.

19 Claims, 3 Drawing Sheets

U.S. PATENT DOCUMENTS

| | | | |
|---|---|---|---|
| 5,417,286 | 5/1995 | Palmer et al. | 166/308 |
| 5,419,396 | 5/1995 | Palmer et al. | 166/250 |
| 5,439,054 | 8/1995 | Chaback et al. | 166/252 |
| 5,454,666 | 10/1995 | Chaback et al. | 405/52 |
| 5,494,108 | 2/1996 | Palmer et al. | 166/308 |
| 5,501,273 | 3/1996 | Puri | 166/252 |
| 5,513,707 | 5/1996 | Shaw et al. | 166/305.1 X |
| 5,669,444 | 9/1997 | Riese et al. | 166/263 |

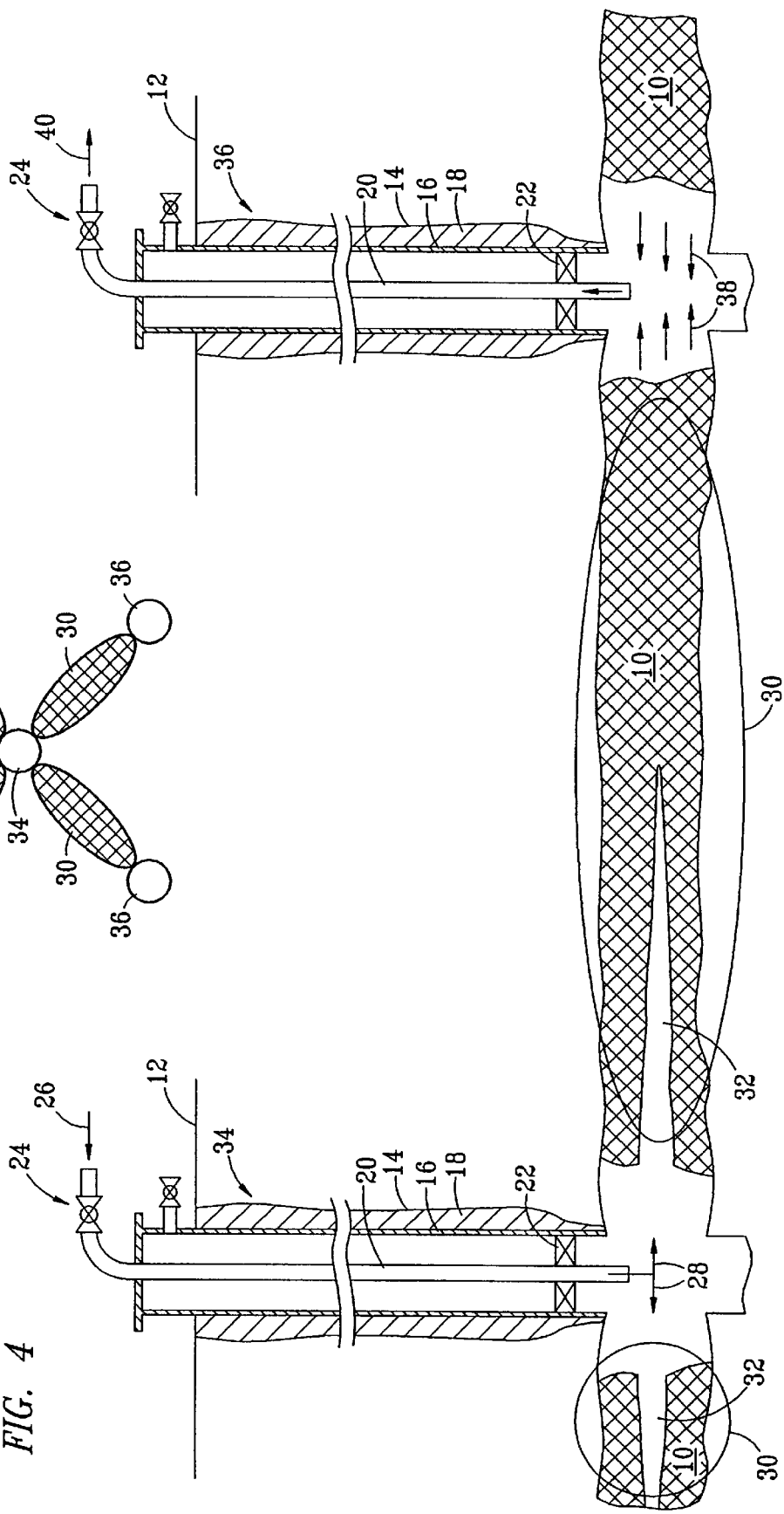

5,865,248

CHEMICALLY INDUCED PERMEABILITY ENHANCEMENT OF SUBTERRANEAN COAL FORMATION

CROSS-REFERENCE TO RELATED APPLICATIONS

This application is a continuation-in-part of U.S. Ser. No. 08/594,725 entitled "Chemically Induced Stimulation of Coal Cleat Formation" filed Jan. 31, 1996, now U.S. Pat. No. 5,669,444, by Walter C. Riese and Stephen V. Bross.

BACKGROUND OF THE INVENTION

1. Field of the Invention

This invention relates to a method for stimulating the formation of cleats in subterranean coal formations and thereby enhancing the relative permeability of existing cleats to both water and gas via chemical treatments. The formation of conductive and contiguous cleat systems within a coal seam is enhanced when the coal matrix is contacted with an oxidative gas. The formation of highly conductive cleat systems allows effective and timely de-watering of the coal formation and increased methane permeability and production and increased ultimate methane recovery. The invention is particularly applicable in coal gas producing areas where production is limited by poor cleat development. The formation of the cleat system also facilitates the completion of wells by cavitation.

2. Brief Description of the Prior Art

Substantial quantities of methane gas are found in subterranean coal formations.

A variety of processes have been used in attempts to recover the methane from the coal formations more efficiently.

The simplest process is the pressure reduction process wherein a borehole is drilled into a coal formation from the surface and methane is withdrawn from the borehole by reducing the pressure to cause methane to be desorbed from and flow from the coal formation into the borehole and to the surface. This method is not efficient because coal formations are generally not extremely porous and the methane is generally not found in the pores of the coal formation but is absorbed onto the coal. While methane can be produced from coal formations by this process, the production of methane is relatively slow.

In some coal formations, the natural permeability is sufficient to allow the removal of in situ water to permit the enhanced recovery of methane. In such formations, cleat systems developed during the coal bed diagenesis provide channel ways through which water and methane migrate to the production wells for removal. This removal of water or "de-watering" of the coal formations removes water from the channel ways and permits the flow of methane through the channel ways and to a production well at a greater rate.

Many coal formations do not have extensively developed cleat systems or have cleat systems which are not fully developed. These coal formations have very low permeability to water and gas and do not yield water or gas at significant rates. As a result, the water fills the channels, and the recovery of methane from such coal formations at significant rates is difficult or impossible. Such low permeability water-containing coal formations may be either water saturated or less than fully water saturated. It appears that coal formations with better developed cleat systems may have been exposed to a diffusive oxidizing fluid of some type during the geologic past whereas coal formations with less developed cleat systems do not show evidence of exposure to an oxidizing fluid in the geologic past.

Accordingly, continuing efforts have been directed to the development of methods for replicating the effects of the conditions in the better developed cleat system coal formations during the geologic past.

SUMMARY OF THE INVENTION

According to the present invention, the rate of recovery of methane from subterranean coal formations is increased by positioning at least one well from the surface into the coal formation; injecting a gaseous oxidant into the coal formation; maintaining the gaseous oxidant in the coal formation; for a selected time to stimulate the formation or enhancement of a cleat system in the coal formation and increase the gas permeability of the coal formation; and, producing methane from the coal formation at an increased rate.

The gaseous oxidant may comprise ozone, oxygen and combinations thereof.

The rate of production of methane and the gas permeability of subterranean coal formations penetrated by at least one injection well and at least one production well is increased by:

a) Injecting a gaseous oxidant into the coal formation through the injection well;

b) maintaining the gaseous oxidant in the coal formation for a selected time to stimulate the formation of cleats in the coal formation; and c) producing methane from the coal formation through the production well at an increased rate.

The completion of wells penetrating a coal seam is facilitated by injecting a gaseous oxidant into the coal formation surrounding the well prior to producing fluids and particulate coal from the coal formation through the well to form a cavity in the coal formation around the well.

BRIEF DESCRIPTION OF THE DRAWINGS

FIG. 4 is a schematic diagram of an injection well and a production well penetrating a subterranean coal formation from the surface wherein the coal formation has been fractured from the injection well.

FIG. 5 is a schematic layout of a 5-spot injection and production well pattern.

DESCRIPTION OF THE PREFERRED EMBODIMENTS

In the discussion of the FIGURES, the same numbers will be used throughout to refer to the same or similar components.

Figure 1:
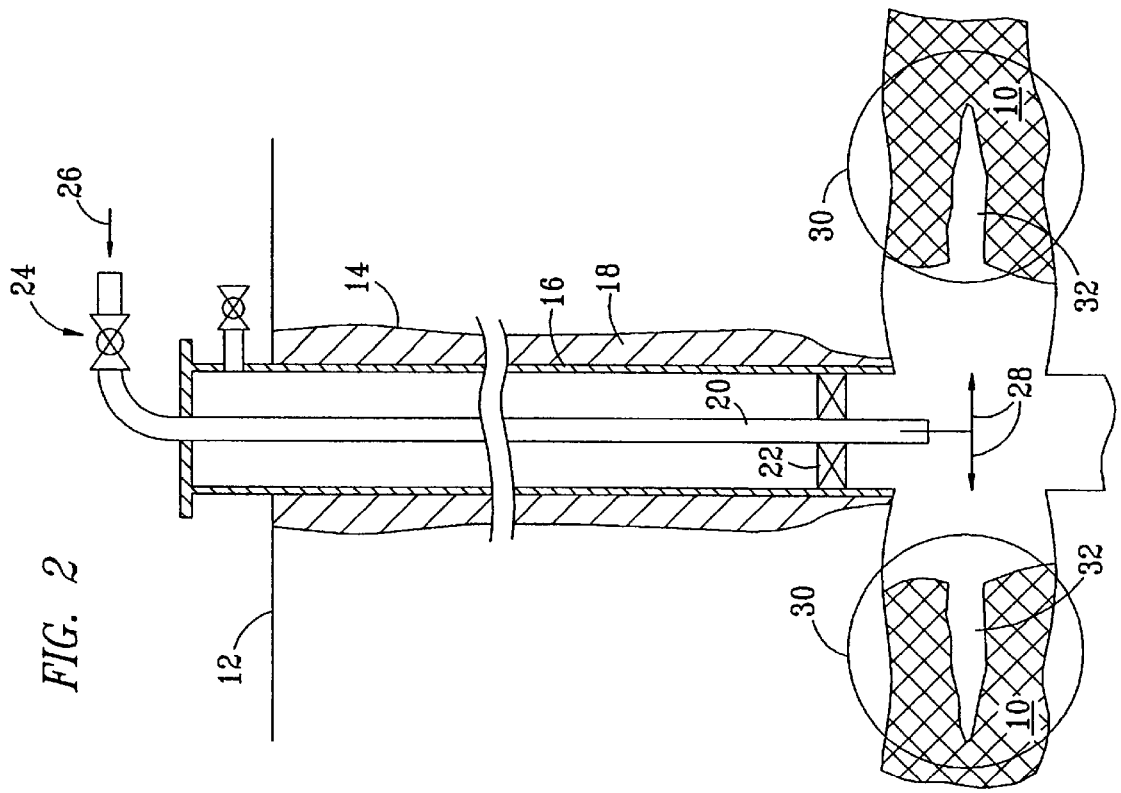
FIG. 1 is a schematic diagram of a well penetrating a subterranean coal formation from the surface.

In FIG. 1, a coal formation 10 penetrated from a surface 12 by a wellbore 14 is shown. The wellbore 14 includes a casing 16 positioned in the wellbore 14 by cement 18. While wellbore 14 is cased it should be understood that in the preferred embodiments shown in the Figures uncased or partially cased wells could be substituted.

The casing 16 could extend into or through the coal formation 10 with perforations through casing 16 in the coal seam providing fluid communication with the coal formation from the casing 16. The wellbore 14 extends into the coal formation 10 and includes a tubing 20 and a packer 22. The packer 22 is positioned to prevent flow between the outer diameter of the tubing 20 and the inner diameter of the casing 16. The wellbore 14 also includes equipment 24 adapted to inject a gaseous or liquid stream into the coal formation 10 or to recover a gaseous or liquid stream from the coal formation 10.

In the practice of the present invention, a gaseous oxidant is injected as shown by an arrow 26 through the tubing 20 into the coal formation 10 as shown by arrows 28. The zones treated are shown by circles 30. The gaseous oxidant is injected into the coal formation 10 for a selected time and in a quantity considered sufficient to enhance or stimulate the formation of a conductive, continuous cleat system in the coal formation 10. After a selected period or after a selected amount of the gaseous oxidant has been injected, the well may be shut in for a period of time, which may be up to or greater than 24 hours. Alternatively, a sufficient period of oxidant presence in the coal formation may have elapsed during the injection of the gaseous oxidant.

Typically, the well is shut-in until the pressure in the wellbore returns to the formation pressure and thereafter for up to 12 additional hours. The shut-in period allows for migration of the oxidant into the coal formation 10 to oxidize components of the coal formation 10 to enhance the cleat system in and increase the gas permeability of the coal formation 10. Subsequent to the shut-in period, water, methane or both may be recovered from the coal formation 10 to de-water the coal formation in the zones 30 and produce methane. The term "de-water" as used herein does not refer to the complete removal of water from the coal formation 10, but rather to the removal of sufficient water from the coal formation 10 to open passage ways in the cleat system in coal formation 10 so that methane can be produced through the passage ways from the coal formation 10.

The gaseous oxidant contains an oxidant selected from the group consisting of ozone, oxygen and combinations thereof. Of these, ozone is preferred. When ozone is used the concentrations may be up to 100 volume percent of the gaseous oxidant mixture.

When oxygen is used the concentrations are suitably up to about 50 percent volume percent of the gaseous oxidant mixture with concentrations up to about 30 volume percent being preferred and with concentrations from about 23 to about 35 volume percent being desirable. The oxygen-containing gaseous oxidant mixture may be air, but is preferably oxygen enriched air containing oxygen at the concentrations stated above. The oxidants can be used in gaseous oxidant mixtures in combination within the ranges discussed above.

Desirably the oxidants are used in gaseous oxidant mixtures as discussed to avoid combustion in the wellbore or coal seam, to avoid gasification or liquification of coal near the wellbore and the like. Applicants seek to physically modify the structure of the coal formation to stimulate the formation of cleats and a cleat system in the coal formation in order to increase the permeability of the formation to gas and liquids while avoiding combustion processes. Application of the gaseous oxidant mixture to the coal formation surfaces, which may be accessed via naturally occurring fractures, artificially created fractures, other existing passageways in the coal formation and the like, provides access to the coal macerals to affect the maceral composition, maceral architecture and bonding between maceral faces thereby stimulating the formation of cleats and a cleat system and increasing the permeability of the coal. This treatment does not result in the removal of coal from the coal formation, or combusion of the coal. Rather the coal structure is modified by creation of the cleats and cleat system to increase the permeability in the coal formation to achieve these objectives without removal of coal from the formation and without gasification or other physical destruction of the coal.

In the embodiment shown in FIG. 1, a single well is used for injection of the gaseous oxidant to chemically enhance or stimulate the formation of a cleat system and increase gas and liquid permeability in the zones 30 to result in an increase in the methane production rate from the coal formation 10. The term "increase" as used herein refers to a change relative to the untreated coal formation.

Figure 2:
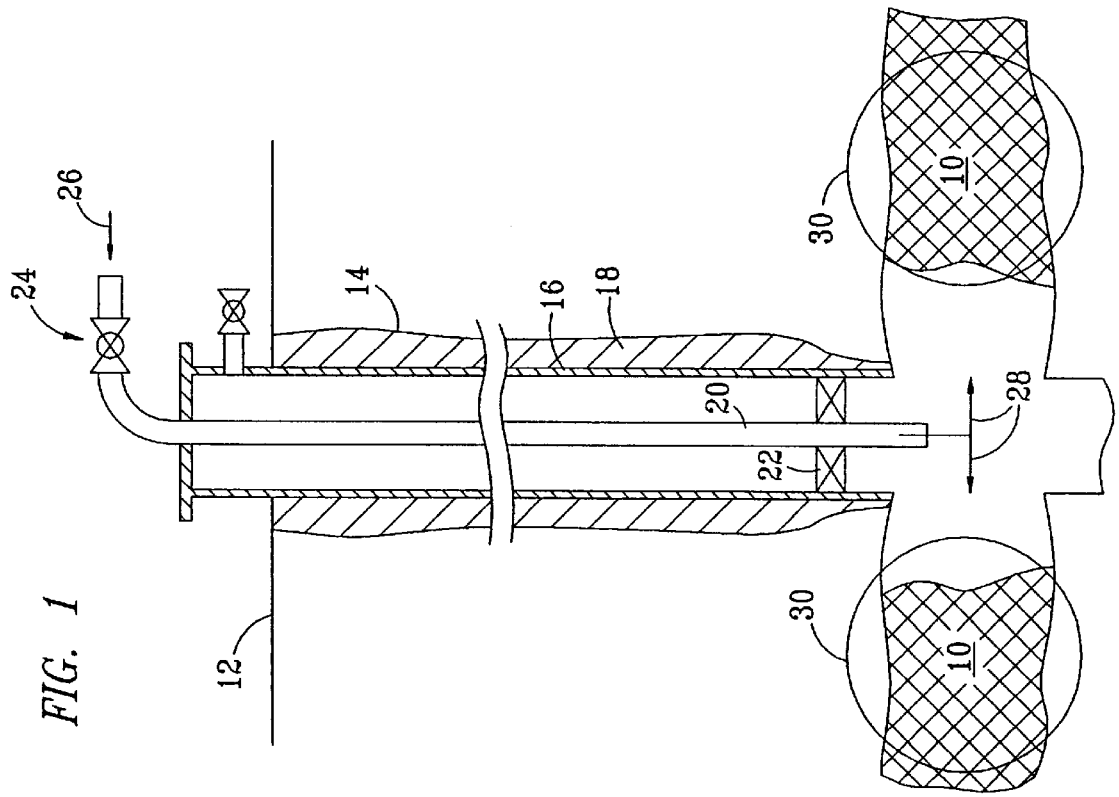
FIG. 2 is a schematic diagram of a well penetrating a subterranean coal formation from the surface wherein the coal formation has been fractured.

In FIG. 2, a similar embodiment is shown except that the coal formation 10 has been fractured by fractures 32. The operation of the well is basically the same as that shown in FIG. 1 except that the coal formation 10 has previously been fractured, or is fractured by a fluid which may include the gaseous oxidant solution during at least part of the fracturing operation. For instance, it may be desirable to use a conventional fracturing application, if the coal formation 10 is sufficiently impermeable, as an initial stimulation method followed by the gaseous oxidant. The gaseous oxidant enhances cleat permeability and increases permeability in areas contacted via the fracture. In such instances, the well may be shut-in as discussed previously and the gaseous oxidants are selected from those discussed previously. The fractures are usually formed in the coal formation 10 prior to injection of the gaseous oxidant. It should also be understood that the gaseous oxidant could also be injected into the coal formation above, below or in the fracture zone.

Figure 3:
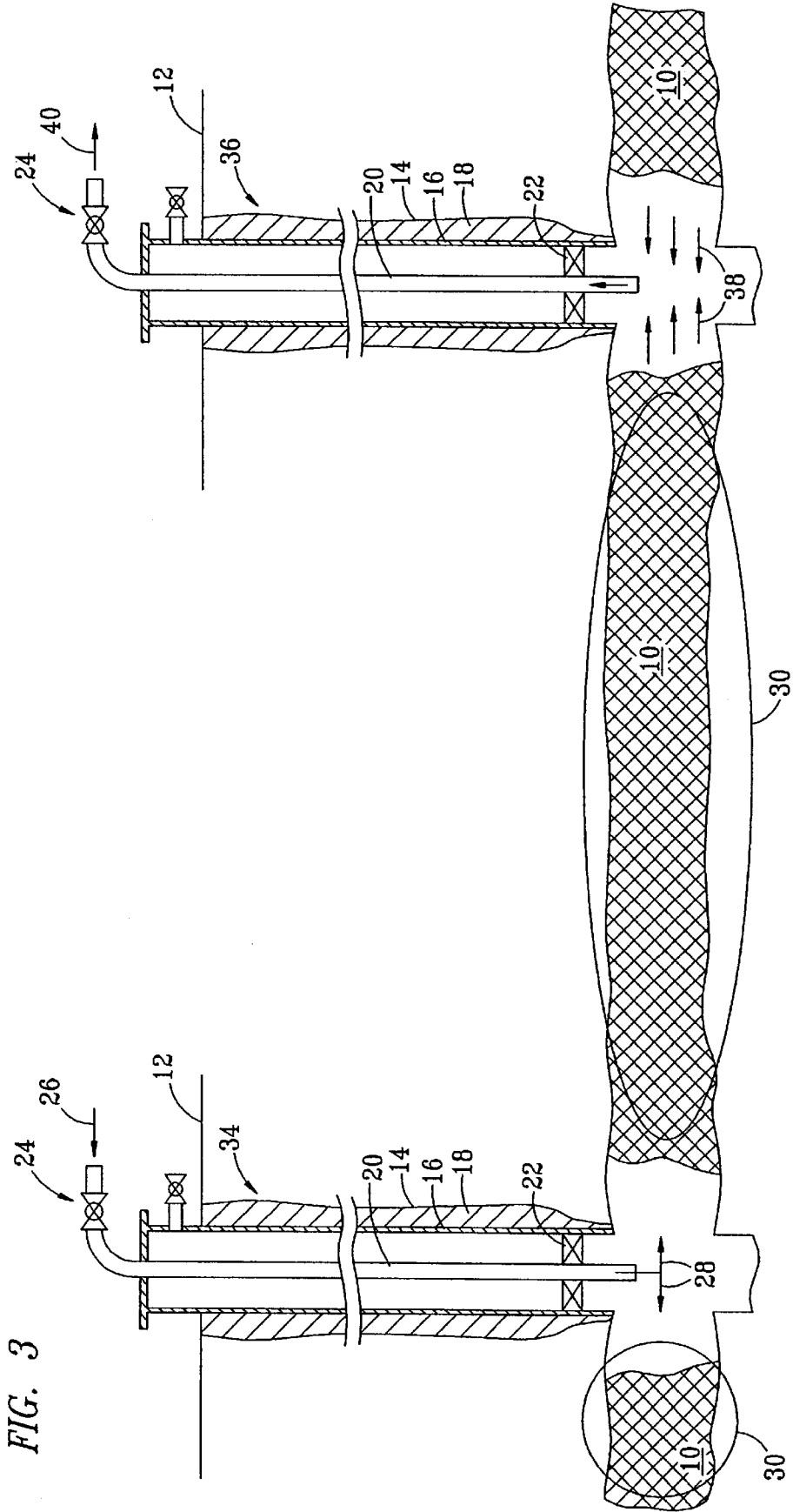
FIG. 3 is a schematic diagram of an injection well and a production well penetrating a subterranean coal formation from the surface.

In FIG. 3, an injection well 34 and a production well 36 penetrate the coal formation 10 from the surface 12. The injection well 34 is spaced apart from the production well 36 at a spacing based upon the characteristics of the particular coal formation and the like. According to the present invention, the gaseous oxidant described above is injected into the coal formation 10 through the injection well 34 as shown by the arrow 26 and the arrows 28 to treat the zones 30 which may extend from the injection well 34 in a generally circumferential direction, but generally extend preferentially toward a nearby production well or production wells.

The production well 36 is positioned to withdraw water, methane or both from the coal formation 10. The production of fluids through the production well 36 causes the gaseous oxidant to migrate toward the production well 36. Desirably, injection of the gaseous oxidant is continued until a desired increase in permeability or an increase in the volume of fluids produced is achieved. The increase in the permeability or volume of fluids produced from the production well 36 is indicative of the formation or enhancement of cleats in the coal formation 10 with a resulting increase in permeability so that additional quantities of fluids are released from the coal formation 10 for production as shown by arrows 38 through the production well 36 and a line 40. The arrows 38 are shown directed toward the production well 36 from both directions in contemplation that fluids will continue to be recovered at a lower rate from untreated portions of the coal formation 10.

The embodiment shown in FIG. 4 is similar to that shown in FIG. 3 except that the coal formation 10 has been fractured by fractures 32. Fractures 32 in the embodiment shown in FIG. 2 can be of substantially any extent. By contrast, in the embodiment shown in FIG. 4, the fractures 32 desirably extend no more than half way to the production well 36. Clearly, if the fractures 32 extend completely into the production well 36, it will be difficult to use any kind of fluid or gas drive between the injection well 34 and the production well 36. The use of the gaseous oxidant with the fractures 32 is as discussed previously.

In FIG. 5, a 5-spot well arrangement is shown. Such well arrangements are useful in the practice of the present invention and may be used in a recurring pattern over a wide area. Such arrangements are well known to those skilled in the art and will be discussed only briefly. In the arrangement shown in FIG. 5, the gaseous oxidant is injected through the injection well 34 to treat the zones 30 to enhance the recovery of fluids and methane from the production wells 36. When the desired cleat formation or permeability increase has been achieved as evidenced by the production of fluids at an increased rate from the production wells 36 or at a selected time the injection of the gaseous oxidant may be stopped and the injection well 34 converted to a production well. The area would then be produced through the original production wells and the converted injection well. The areas of enhanced cleat formation will increase the methane production rates and the ultimate methane recovery.

In many instances wells in coal formations are completed by "cavitation" of the coal seam to produce a cavity surrounding the well. Such completion techniques are disclosed in U.S. Pat. No. 5,417,286, "Method For Enhancing The Recovery of Methane From A Solid Carbonaceous Subterranean Formation", issued May 23, 1995 to Ian D. Palmer and Dan Yee and SPE 24906, "Openhole Cavity Completions in Coalbed Methane Wells in the San Juan Basin" presented Oct. 4–7, 1992 by I. D. Palmer, M. J. Mavor, J. P. Seidle, J. L. Spitler and R. F. Volz. U.S. Pat. No. 5,417,286 is hereby incorporated in its entirety by reference. In some instances the coal formation penetrated by the well may not readily cavitate upon production of fluids from the coal formation. In such instances injection of the gaseous oxidant to develop cleats in the coal formation surrounding such wells can be used to weaken the coal formation and facilitate the initiation of cavitation.

Cavitation as used herein refers to formation of an openhole interval cavity as described in U.S. Pat. No. 5,417,286 previously incorporated by reference at column 1, line 50 through column 2, line 2 as follows.

'One example of a technique for stimulating the production of methane from a solid carbonaceous subterranean formation is to complete the production wellbore with an open-hole cavity. First, a wellbore is drilled to a location above the solid carbonaceous subterranean formation. The wellbore is cased and the casing is cemented in place using a conventional drilling rig. A modified drilling rig is then used to drill an "open-hole" interval within the formation. An open-hole interval is an interval within the solid carbonaceous subterranean formation which has no casing set. A metal liner, which has holes, may be placed in the open-hole interval if desired. The open-hole interval can be completed by various methods. One method utilizes an injection/ blowdown cycle to create a cavity within the open-hole interval. In this method, air is injected into the open-hole interval and then released rapidly through a surface valve. The procedure is repeated until a suitable cavity has been created. During the procedure, a small amount of water can be added to selected air injections to reduce the potential for spontaneous combustion of the carbonaceous material of the formation.'

The method of the present invention is also useful as a pre-treatment for gas injection treatments to enhance the recovery of methane from the coal formation 10. The use of carbon dioxide, either alone or with other gases, to increase the production of methane from coal formations is well known. Similarly, the use of inert gases, such as nitrogen, argon and the like, to remove additional quantities of methane from coal formations by increasing the pressure in the formation and thereby removing additional methane as the methane partial pressure in the atmosphere in the coal seam is decreased are well known to those skilled in the art. The use of such processes requires that the formation be permeable to gas flow into or through the formation so that the methane can be recovered. The method of the present invention enhances the permeability of coal formations and may be used prior to the use of gas sweep or gas desorbtion treatments to enhance the recovery of methane.

Having thus described the present invention by reference to certain of its preferred embodiments, it is noted that the embodiments discussed are illustrative rather than limiting in nature and that many variations and modifications are possible within the scope of the present invention. Many such variations and modifications maybe considered obvious and desirable by those skilled in the art based upon a review of the foregoing description of preferred embodiments.

Having thus described the invention, we claim:

1. A method of increasing the gas permeability of a subterranean coal formation penetrated by at least one well, the method comprising:

a) injecting a gaseous oxidant into the coal formation;
   b) maintaining at least a portion of the gaseous oxidant in the coal formation for a selected time to stimulate the formation of cleats in the coal formation; and
   c) producing methane from the coal formation at an increased rate.

2. The method of claim 1 wherein the gaseous oxidant comprises a gaseous oxidant selected from the group consisting of ozone, oxygen and combinations thereof.

3. The method of claim 2 wherein the gaseous oxidant comprises ozone.

4. The method of claim 3 wherein the ozone is diluted with an inert gaseous diluent to form a gaseous oxidant mixture containing up to about 100 volume percent ozone.

5. The method of claim 2 wherein the gaseous oxidant comprises oxygen.

6. The method of claim 5 wherein the oxygen is diluted with an inert diluent to form a gaseous oxidant mixture containing 23 to 35 volume percent oxygen.

7. The method of claim 5 wherein the gaseous oxidant is air.

8. The method of claim 5 wherein the gaseous oxidant is oxygen-enriched air.

9. The method of claim 8 wherein the oxygen-enriched air contains at least about 30 volume percent oxygen.

10. The method of claim 8 wherein oxygen-enriched air contains at least about 50 volume percent oxygen.

11. The method of claim 1 wherein the gaseous oxidant is injected into the coal formation through a well; the well is shut-in for a selected time; and thereafter, methane is produced from the well at an increased rate.

12. A method for increasing the gas permeability of a subterranean coal formation penetrated by at least one injection well and at least one production well, the method comprising:

a) injecting a gaseous oxidant into the coal formation through the injection well;
b) maintaining the gaseous oxidant in the coal formation for a selected time to stimulate the formation of cleats in the coal formation; and thereafter
c) producing methane from the coal formation through the production well at an increased rate.

13. The method of claim 12 wherein the gaseous oxidant comprises an oxidant selected from the group consisting of ozone, oxygen and combinations thereof.

14. The method of claim 12 wherein the oxidant comprises ozone.

15. A method for completing a well penetrating a subterranean coal formation with an open hole cavity, the method consisting essentially of:
   a. injecting a gaseous oxidant selected from the group consisting of ozone or a gaseous mixture containing from about 23 to about 35 volume percent oxygen and mixtures thereof into the coal formation through the well;
   b. rapidly releasing the gaseous oxidant from the coal formation through the well, thereby forming a cavity in the coal formation around the well.

16. A method for completing a well penetrating a subterranean coal formation with an open hole cavity, the method consisting essentially of:
   a. injecting a gaseous oxidant into the coal formation through the well; and
   b. shutting in the well for a shut-in period to permit the pressure in the well to increase and thereafter opening the well for a production period to permit a flow of fluids from the coal formation through the well.

17. The method of claim 16 wherein a plurality of shut-in periods and production periods are used to form the cavity.

18. The method of claim 15 wherein the gaseous oxidant is injected into the coal formation during an injection period to increase the pressure in the coal formation around the well and thereafter the well is opened for a production period to permit the flow of the gaseous oxidant from the coal formation through the well to form the cavity.

19. The method of claim 13 wherein the gaseous oxidant is oxygen-enriched air.

* * * * *